(12) United States Patent
Bardsley et al.

(10) Patent No.: US 7,615,661 B2
(45) Date of Patent: Nov. 10, 2009

(54) THIOESTER COMPOUNDS AND THEIR USE IN FRAGRANCE OR FLAVOR APPLICATIONS

(75) Inventors: Kathryn Bardsley, Staten Island, NY (US); David O. Agyemang, Jackson, NJ (US); Tao Pei, Morganville, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 12/047,095

(22) Filed: Mar. 12, 2008

(65) Prior Publication Data

US 2009/0232747 A1 Sep. 17, 2009

(51) Int. Cl.
*C07C 205/00* (2006.01)
*C07C 315/00* (2006.01)
*C07C 325/00* (2006.01)
*A23L 1/26* (2006.01)

(52) U.S. Cl. .................... 560/125; 560/152; 568/18; 568/20; 426/535

(58) Field of Classification Search ............... 560/125; 568/18, 20
See application file for complete search history.

(56) References Cited

U.S. PATENT DOCUMENTS

| | | | |
|---|---|---|---|
| 3,994,997 A | 11/1976 | Singerman | |
| 4,426,403 A | 1/1984 | Cyronak et al. | |
| 5,719,168 A * | 2/1998 | Laurent | 514/357 |
| 6,359,009 B1 * | 3/2002 | Diehl et al. | 514/621 |
| 6,589,969 B1 | 7/2003 | Tajima et al. | |
| 6,821,994 B2 | 11/2004 | Tajima et al. | |
| 2004/0209920 A1 | 10/2004 | Stapper | |
| 2005/0101637 A1 | 5/2005 | Stapper | |
| 2005/0215596 A1 | 9/2005 | Stapper | |

OTHER PUBLICATIONS

Zhou et al. Tripodal Bis(imidazole) Thioether Copper (I) Complexes: Mimics of the Cu M Site of Copper Hydroxylase Enzymes. Inorganic Chemistry, 2007 vol. 46 (19), 7789-7799.*

* cited by examiner

*Primary Examiner*—Sikarl A Witherspoon
(74) *Attorney, Agent, or Firm*—Elizabeth M. Quirk; XuFan Tseng; Joseph F. Leightner

(57) ABSTRACT

The present invention relates to thioester compounds and the incorporation and use of the new chemical entities as flavor and fragrance chemicals.

8 Claims, No Drawings

THIOESTER COMPOUNDS AND THEIR USE IN FRAGRANCE OR FLAVOR APPLICATIONS

FIELD OF THE INVENTION

The present invention relates to thioester compounds and the incorporation and use of the new chemical entities as flavor and fragrance chemicals.

BACKGROUND OF INVENTION

There is an ongoing need in the flavor and fragrance industry to provide new chemicals to give perfumers and other persons ability to create new fragrances for perfumes, colognes and personal care products.

Thiols are known to yield very powerful and consequentially very foul odors. In studying chemical structures and their structure reactivity relationships, it was suspected that certain functional groups bring out a more pleasant thiol aroma and at the same time maintain odor and taste strength. Esters are widely used in flavors and fragrances. With increasing knowledge of synergy exerted between certain functional groups, there is an ongoing need to be able to produce other related compounds to determine if these compounds have unique properties and if these compounds are suitable for incorporation in flavor and fragrance formulations.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the novel compounds, represented by Formula I set forth below:

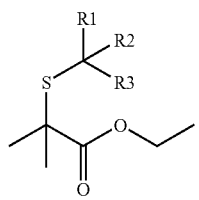

Formula I wherein $R^1$, $R^2$ and $R^3$ is independently selected from a $C_1$ to $C_4$ hydrocarbon moiety that may be straight, branched or cyclic and may contain single and/or double bonds; and wherein $R^1$ and $R^2$ taken together can be equal to oxygen, herein referred to as O, and $R^3$ can be a H, methyl, ethyl or a $C_4$ to $C_7$ cyclic hydrocarbon.

In another embodiment, the invention is also directed to a method of flavoring a product by adding to the product of at least one thioester defined according to Formula I.

The invention is also directed to a food or beverage product containing a flavor/aroma composition comprising a at least one thioester defined according to Formula I.

In an additional embodiment, the invention is also directed to a method of flavoring a product by adding to the product at least one thioester defined according to Formula II,

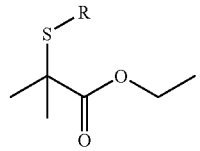

Formula II wherein R is a hydrogen or a $C_1$ to $C_4$ straight, branched or cyclic hydrocarbon moiety containing single and/or double bonds in an amount effective to flavor the product.

The invention is also directed to a food or beverage product containing a flavor/aroma composition comprising a at least one thioester defined according to Formula II.

The invention is also directed to a flavor composition containing one or a combination of these compounds. The compound in the flavor composition is at a concentration in the range of about 0.01 ppb to 50 ppm. The invention is also directed to a food or beverage product containing the above flavor compositions.

The invention is further directed to a method of flavoring a product, such as a food, beverage, oral hygiene product, pharmaceutical, or chewing gum, by adding one or a combination of the above compounds in an amount sufficient to flavor the product. The concentration of the compound may be in the range of about 0.01 ppb to 50 ppm.

These and other embodiments of the present invention will be apparent by reading the following specification.

DETAILED DESCRIPTION OF THE INVENTION

According to one embodiment of the present invention the following compounds are provided,

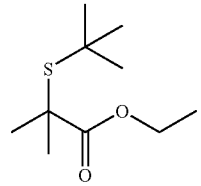

Structure III

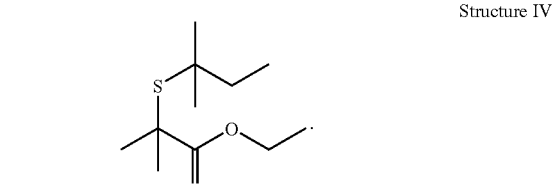

Structure IV

Structures III and IV are also known by one skilled in the art as 2-t-Butylsulfanyl-2-methyl-propionic acid ethyl ester and 2-(1,1-Dimethyl-propylsulfanyl)-2-methyl-propionic acid ethyl ester respectively.

In a further embodiment of the invention the use of the following compound in flavor and fragrance applications is disclosed:

Structure V

Structure V is known by one skilled in the art as 2-methyl-2-(methylthio)-propanoic acid ethyl ester.

The compounds of the present invention may be prepared from the corresponding general reaction scheme detailed below and R is a hydrogen or a $C_1$ to $C_4$ alkyl, such as methyl, ethyl, propyl and butyl:

Formula II

In one embodiment of the invention, compounds Structure III and Structure IV are prepared according to the following reaction scheme:

Structure III and

Structure IV

In an additional embodiment of the invention, Structure XI known by one skilled in the art as Ethyl 2-(Benzoylthio)-2-methyl propanoate is prepared according to the following reaction scheme for which the details of the reaction are provided in Example II.

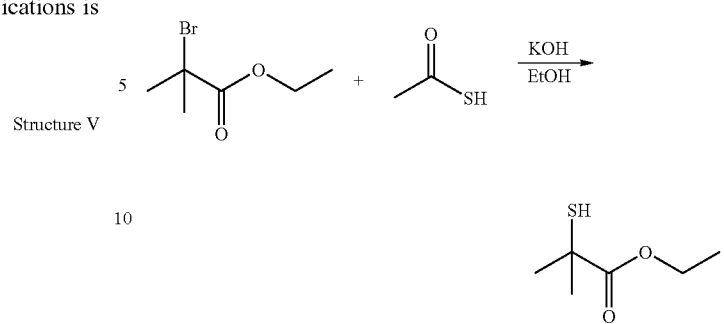

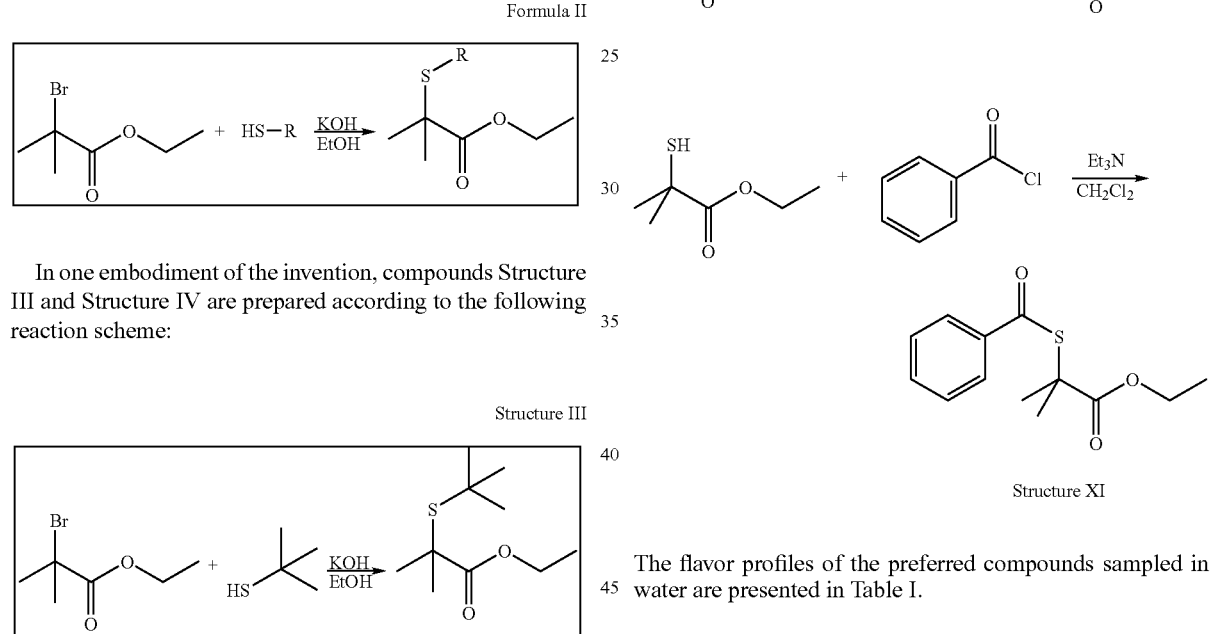

Structure XI

The flavor profiles of the preferred compounds sampled in water are presented in Table I.

TABLE I

| Compound | Wt %. | Flavor Profile |
|---|---|---|
|  Structure III | 1 ppm | Green, ocimene, pineapple, mango, over ripe pineapple, green banana |
| Structure IV | 5 ppm | Grape skin, grapefruit, catty, tropical |

TABLE I-continued

| Compound | Wt %. | Flavor Profile |
|---|---|---|
| 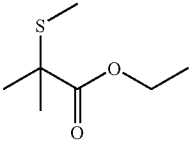 Structure V | 10 ppm | Savory, bloody, juicy meat, tropical |
| 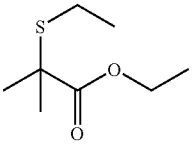 Structure VII | 2 ppm | Fruity, tropical, strawberry, mango, dirty, sweet |
| 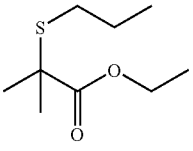 Structure VIII | 100 ppb | Cabbage, ocimene, Mexican mango, tropical |
| 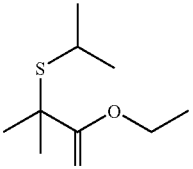 Structure X | 10 ppm | Meaty and bloody |

It is known by one skilled in the art that Structure III is 2-t-Butylsulfanyl-2-methyl-propionic acid ethyl ester; Structure IV is 2-(1,1-Dimethyl-propylsulfanyl)-2-methyl-propionic acid ethyl ester; Structure V is 2-methyl-2-(methylthio)-propanoic acid ethyl ester; Structure VII 2-Ethylthio-2-methyl-propionic acid ethyl ester and Structure VIII is 2-Methyl-2-propylthio-propionic acid ethyl ester and Structure X is 2-Isopropylsulfanyl-2-methyl-propionic acid ethyl ester.

As used herein olfactory effective amount is understood to mean the amount of compound in flavor compositions the individual component will contribute to its particular olfactory characteristics, but the flavor, taste and aroma effect on the overall composition will be the sum of the effects of each of the flavor ingredients. As used herein taste effects include salt and umami, effects. Thus the compounds of the invention can be used to alter the taste characteristics of the flavor composition by modifying the taste reaction contributed by another ingredient in the composition. The amount will vary depending on many factors including other ingredients, their relative amounts and the effect that is desired.

Based on their clear fruity organoleptic properties, the compounds are suitable for the creation of flavor and fragrance compositions. They can be combined in the usual manner with practically all available flavor or fragrance raw materials, i.e. synthetic and/or nature identical and/or natural substances and/or natural extracts and/or additional carrier materials and/or further additives used in the flavor or fragrance field.

Specifically, the very distinct berry and estery floral notes of the compounds according to the invention enable the production of specific and characteristic flavor profiles, which are new. These can be used for the aromatization of foodstuffs, beverages, pharmaceuticals, oral hygiene products (e.g. toothpaste) or other healthcare products.

Further, specifically the compounds of the invention add a berry, fruity and some tropical aspects to fruit flavor compositions such as peach, strawberry, passion fruit, citrus and raspberry. Thereby the body of the flavor is increased and its stability (i.e., longevity) improved. However, use is not restricted to fruit flavors, as the inventive compounds can also be combined also with herbal, mint and savory flavors, whereby they especially increase the fullness, freshness and/or the herbal character. For example, in meat flavors, they increase the natural meat aroma.

Due to their fruity odor characteristics, the compounds of the invention can also be used in fragrance compositions such as fine fragrances or perfumed products of all kinds, especially cosmetic articles, consumer healthcare or household products as, e.g., washing agents, detergents, soaps or toothpaste. Here, specifically, the inventive compounds add an herbal-fruity and, surprisingly, also a marine aspect to floral, musk and woody accords. At the same time the freshness is increased.

Instead of directly using a compound of the invention as a flavor or fragrance ingredient, it may be advantageous to use a precursor thereof, i.e. a chemical derivative of a compound according to the invention which can be easily transformed to the compound according to the invention. The precursors also have sensorial interest. For example, and preferably, as precursors the esters of 3-acylthio acids, which can be obtained by treatment of the compounds according to the invention with acyl chloride, may be added to an aroma or food or fragrance composition. From the esters of 3-acylthioacids, the inventive compounds can be released by enzymatic hydrolysis and/or chemical treatment. This reaction can take place either in the flavor or fragrance composition, or in the products containing these compositions.

The term "product" as used herein includes both solid and liquid ingestible materials for man or animals, which materials usually do, but need not, have nutritional value. Thus, products include foods, such as but not limited to, meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products an oral hygiene product, a pharmaceutical, a chewing gum, and combinations thereof.

When the compounds of this invention are used in a flavoring composition, they can be combined with conventional flavoring materials or adjuvants. Such co-ingredients or flavor adjuvants are well known in the art for such use and have been extensively described in the literature. Requirements of such adjuvant materials are: (1) that they be non-reactive with the compounds of our invention; (2) that they be organoleptically compatible with the compounds derivative(s) of our invention whereby the flavor of the ultimate consumable material to which the compounds are added is not detrimentally affected by the use of the adjuvant; and (3) that they be ingestible acceptable and thus nontoxic or otherwise non-deleterious. Apart from these requirements, conventional materials can be used and broadly include other flavor materials, vehicles, stabilizers, thickeners, surface active agents, conditioners and flavor intensifiers.

Such conventional flavoring materials include saturated fatty acids, unsaturated fatty acids and amino acids; alcohols including primary and secondary alcohols, esters, carbonyl compounds including ketones, other than the alkyldienamides of our invention and aldehydes; lactones; other cyclic organic materials including benzene derivatives, acyclic compounds, heterocyclics such as furans, pyridines, pyrazines and the like; sulfur-containing compounds including thiols, sulfides, disulfides and the like; proteins; lipids, carbohydrates; so-called flavor potentiators such as monosodium glutamate; magnesium glutamate, calcium glutamate, guanylates and inosinates; natural flavoring materials such as hydrolyzates, cocoa, vanilla and caramel; essential oils and extracts such as anise oil, clove oil and the like and artificial flavoring materials such as vanillin, ethyl vanillin and the like.

Specific preferred flavor adjuvants include but are not limited to the following: anise oil; ethyl-2-methyl butyrate; vanillin; cis-3-heptenol; cis-3-hexenol; trans-2-heptenal; butyl valerate; 2,3-diethyl pyrazine; methyl cyclo-pentenolone; benzaldehyde; valerian oil; 3,4-dimethoxy-phenol; amyl acetate; amyl cinnamate; γ-butyryl lactone; furfural; trimethylpyrazine; phenyl acetic acid; isovaleraldehyde; ethyl maltol; ethyl vanillin; ethyl valerate; ethyl butyrate; cocoa extract; coffee extract; peppermint oil; spearmint oil; clove oil; anethol; cardamom oil; wintergreen oil; cinnamic aldehyde; ethyl-2-methyl valerate; γ-hexenyl lactone; 2,4-decadienal; 2,4-heptadienal; methyl thiazole alcohol (4-methyl-5-β-hydroxyethyl thiazole); 2-methyl butanethiol; 4-mercapto-2-butanone; 3-mercapto-2-pentanone; 1-mercapto-2-propane; benzaldehyde; furfural; furfuryl alcohol; 2-mercapto propionic acid; alkyl pyrazine; methyl pyrazine; 2-ethyl-3-methylpyrazine; tetramethylpyrazine; polysulfides; dipropyl disulfide; methyl benzyl disulfide; alkyl thiophene; 2,3-dimethyl thiophene; 5-methyl furfural; acetyl furan; 2,4-decadienal; guiacol; phenyl acetaldehyde; β-decalactone; d-limonene; acetoin; amyl acetate; maltol; ethyl butyrate; levulinic acid; piperonal; ethyl acetate; n-octanal; n-pentanal; n-hexanal; diacetyl; monosodium glutamate; monopotassium glutamate; sulfur-containing amino acids, e.g., cysteine; hydrolyzed vegetable protein; 2-methylfuran-3-thiol; 2-methyldihydrofuran-3-thiol; 2,5-dimethylfuran-3-thiol; hydrolyzed fish protein; tetramethylpyrazine; propylpropenyl disulfide; propylpropenyl trisulfide; diallyl disulfide; diallyl trisulfide; dipropenyl disulfide; dipropenyl trisulfide; 4-methyl-2-[(methylthio)-ethyl]-1,3-dithiolane; 4,5-dimethyl-2-(methylthiomethyl)-1,3-dithiolane; and 4-methyl-2-(methylthiomethyl)-1,3-dithiolane. These and other flavor ingredients are provided in U.S. Pat. Nos. 6,110,520 and 6,333,180 hereby incorporated by reference.

The compounds of our invention or compositions incorporating them, as mentioned above, can be combined with one or more vehicles or carriers for adding them to the particular product. Vehicles can be edible or otherwise suitable materials such as ethyl alcohol, propylene glycol, water and the like, as described supra. Carriers include materials such as gum arabic, carrageenan, xanthan gum, guar gum and the like.

The thioester prepared according to our invention can be incorporated with the carriers by conventional means such as spray-drying, extrusion, drum-drying and the like. Such carriers can also include materials for coacervating the thioesters of our invention to provide encapsulated products, as set forth supra. When the carrier is an emulsion, the flavoring composition can also contain emulsifiers such as mono- and diglycerides or fatty acids and the like. With these carriers or vehicles, the desired physical form of the compositions can be prepared.

The quantity of thioester utilized should be sufficient to impart the desired flavor characteristic to the product, but on the other hand, the use of an excessive amount of thiols is not only wasteful and uneconomical, but in some instances, too large a quantity may unbalance the flavor or other organoleptic properties of the product consumed. The quantity used will vary depending upon the ultimate product the amount and type of flavor initially present in the product; the further process or treatment steps to which the product will be subjected; regional and other preference factors; the type of storage, if any, to which the product will be subjected; and the preconsumption treatment such as baking, frying and so on, given to the product by the ultimate consumer. Accordingly, the terminology "effective amount" and "sufficient amount" is understood in the context of the present invention to be quantitatively adequate to alter the flavor of the product.

The preferred dosage range of the compounds according to the invention in product is from 0.001 ppm to 500 ppm, preferably 0.01 ppm to 50 ppm. Thus, a flavor composition may contain one or more compounds according to the invention. The total content of one or more of these compounds is preferably in the range of 0.001 ppm to 500 ppm and preferably in the range of 0.01 ppm to 5 ppm, depending on the product to be flavored.

In fragrance compositions, concentrations of the inventive compound(s) from 0.001% to 30%, preferably from 0.01% to 10%, are preferably used.

The following are provided as specific embodiments of the present invention. Other modifications of this invention will be readily apparent to those skilled in the art. Such modifications are understood to be within the scope of this invention. All starting materials, reagents and catalysts were purchased from Aldrich Chemical Company and used as is. As used herein all percentages are weight percent unless otherwise noted, ppm is understood to stand for parts per million, L is understood to be liter, mL is understood to be milliliter, Kg is understood to be kilogram, g is understood to be gram, and mmHg be millimeters (mm) of mercury (Hg). IFF as used in the examples is understood to mean International Flavors & Fragrances Inc., New York, N.Y., USA.

Example 1

Preparation of Thioesters

The following reaction sequence was used to prepare the specific compounds described by the NMR data set forth below:

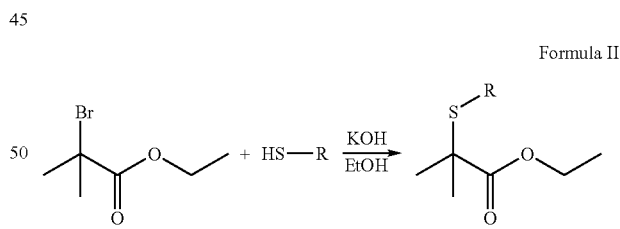

Formula II

Using an ice bath, potassium hydroxide pellets (88%) were added to ethanol (<10° C.) in a three-neck round-bottomed flask with stirring until all of the potassium hydroxide had dissolved. The thiol was added dropwise over a period of 10-15 minutes stirring the reaction mixture for an additional 10 minutes following the addition. Ethyl 2-bromoisobutyrate was slowly added dropwise over 30-60 minutes maintaining temperature <10° C. White precipitate was observed. The resulting mixture was left to age for approximately 15 minutes then gradually heated to reflux (77-78° C.) for 1 to 6 hours. The reaction mixture was cooled to room temperature, quenched with water, extracted using MTBE (in one case ethyl acetate), washed with saturated sodium chloride solu-

Structure I: 2-Mercapto-2-methyl-propionic acid ethyl ester

Ethyl 2-bromoisobutyrate (48.8 g, 0.250 mole), sodium hydrosulfide hydrate (84 g, 1.5 mole), water (100 mL), ethyl alcohol (200 mL). Let reaction mix stir at room temperature. Next day, no starting material observed. Crude yield: 74.3%; distillation yield: 36.0%.

Flavor description: Passionfruit, red fruit, catty, cassis, red currant, oily, mouthfeel (coating), tropical, coffee, tropical, blackcurrant, fresh onion, peach.

Fragrance description: tropical, passionfruit, onion, catty, fruity, natural cassis.

HMNR: 1.29 ppm (t, 3H, J=7.12 Hz); 1.59 ppm (s, 6H); 2.44 ppm (s, 1H); 4.19 ppm (q, 2H, J=7.12 Hz).

Structure II: 2-Allylsulfanyl-2-methyl-propionic acid ethyl ester

Ethyl 2-bromoisobutyrate (40.0 g, 0.205 mole), allyl mercaptan (16.8 g, 0.0226 mole), potassium hydroxide (14.4 g, 0.226 mole), ethyl alcohol (100 g) were combined and reaction mixture was refluxed for six hours prior to quenching. Crude yield: 79.3%; Distilled yield: 35.0%.

Flavor description: onion, vegetative, papaya.

Fragrance description: onion, vegetative.

HMNR: 1.29 ppm (t, 3H, J=7.12 Hz), 1.52 ppm (s, 6H), 3.29 ppm (d, 2H, J=7.01 Hz), 4.17 ppm (q, 2H, J=7.12 Hz), 5.06 ppm (d, 1H, J=10.01 Hz), 5.19 ppm (d, 1H, J=16.96 Hz), 5.82 ppm (m, 1H).

Structure III: 2-t-Butylsulfanyl-2-methyl-propionic acid ethyl ester

Ethyl 2-bromoisobutyrate (40.0 g, 0.205 mole), 2-methyl-2-propanethiol (20.4 g, 0.0226 mole), potassium hydroxide (14.4 g, 0.226 mole), ethyl alcohol (100 g) were combined and reaction mixture was refluxed for six hours prior to quenching. Crude yield: 61.0%; Distilled yield: 34.7%. Flavor description: astringent, tropical, mango, citrus, grapefruit, onion, catty, marigold, herbal, floral, geranium, green. Fragrance description: grapefruit, passion fruit, papaya, dandelion, marigold, caraway, berries, slight onion.

HMNR: 1.46 ppm (pentet, 2H, J=5.58 Hz), 1.50 ppm (s, 6H), 1.63 ppm (pentet, 4H, J=5.68 Hz), 2.58 ppm (m, 4H).

Structure IV: 2-(1,1-Dimethyl-propylsulfanyl)-2-methyl-propionic acid ethyl ester Ethyl 2-bromoisobutyrate (33.9 g, 0.174 mole), 2-methyl-2-butanethiol (20.0 g, 0.192 mole), potassium hydroxide (12.2 g, 0.192 mole), ethyl alcohol (100 g) were combined and the reaction mixture was refluxed for approximately 10 hours prior to quenching. Crude yield: 63.5%; after column chromatography 18.1%.

Flavor description: tropical, catty. Fragrance description: cassis, powerful.

HMNR: 0.94 ppm (t, 3H, J=7.42 Hz); 1.30 ppm (t, 3H, J=7.12 Hz); 1.30 ppm (s, 6H); 1.56 ppm (s, 6H); 1.59 ppm (q, 2H, J=7.39 Hz); 4.17 ppm (q, 2H, J=7.13 Hz).

Structure V: 2-methyl-2-(methylthio)-propanoic acid ethyl ester

Ethyl 2-bromoisobutyrate (40.0 g, 0.205 mole), methanethiol (1.09 g, 0.0226 mole), potassium hydroxide (14.4 g, 0.226 mole,), ethyl alcohol (100 g), refluxed reaction mixture until peak for ethyl 2-bromoisobutyrate is no longer detectable by gas chromatography. Distill to purify.

Flavor description: cocoa, waxy, cheesy, mouthfeel, freezer burn. Fragrance description: mango, green, peach, cassis.

Structure VII: 2-Ethylthio-2-methyl-propionic acid ethyl ester

Ethyl 2-bromoisobutyrate (28.6, 0.146 mole), ethanethiol (100 g, 0.161 mole), potassium hydroxide (10.3 g, 0.161 mole), ethyl alcohol. Stirred reaction mixture for two hours at room temperature prior to quenching. Crude yield: 117%; after kugelrohr: 77.8%.

Flavor description: cabbage water. Fragrance description: Onion, chemical.

HMNR: 1.21 ppm (t, 3H, J=7.50 Hz); 1.28 ppm (t, 3H, J=7.12 Hz); 1.51 ppm (s, 6H); 2.63 ppm (q, 2H, J=7.50 Hz); 4.18 ppm (q, 2H, J=7.11 Hz).

Structure VIII: 2-Methyl-2-propylthio-propionic acid ethyl ester

Ethyl 2-bromoisobutyrate (58.6 g, 0.30 mole), propanethiol (25.0 g, 0.33 mole), potassium hydroxide (21.0 g, 0.33 mole), ethyl alcohol (100 mL). Stirred reaction mixture for one hour at room temperature prior to quenching. Crude yield: 91.2%; distilled yield: 42.1%. Flavor description: green, melon, cantaloupe, tropical, soft syrupy mouthfeel, catty, fruity, parsley, herbaceous, meaty, beefy, canned peach.

Fragrance description: tropical, sulfury, catty, grapefruit, mango, peach, cucumber, beef, green, fruity, dirty, herbal.

HMNR: 0.97 ppm (t, 3H, J=7.36 Hz); 1.28 ppm (t, 3H, J=7.12 Hz); 1.50 ppm (s, 6H); 1.56 ppm (hextet, 2H, J=7.34 Hz); 2.58 ppm (t, 2H, J=7.38 Hz); 4.17 ppm (q, 2H, J=7.12 Hz).

Structure IX: 2-Methyl-2-phenylsulfanyl-propionic acid ethyl ester

Ethyl 2-bromoisobutyrate (40.0 g, 0.205 mole), thiophenol (24.9 g, 0.0226 mole), potassium hydroxide (14.4 g, 0.226 mole), ethyl alcohol (100 g) were combined and reaction mixture was refluxed for six hours prior to quenching. Yield: 76.5%.

Flavor description: floral, tea, slight lemon, fresh grapefruit, woody, rosy, tropical, fruity, cinnamate, green, mango, onion.

Fragrance description: floral, sweet, slight meaty, caraway, phenyl ester, tropical, grapefruit, onion, garlic.

HMNR: 1.20 ppm (t, 3H, J=7.14 Hz), 1.49 ppm (s, 6H), 4.10 ppm (q, 2H, J=7.14 Hz), 7.35-7.48 ppm (m, 5H).

Structure X: 2-Isopropylsulfanyl-2-methyl-propionic acid ethyl ester

Ethyl 2-bromoisobutyrate (100 g, 0.513 mole), 2-propanethiol (42.95 g, 0.564 mole), potassium hydroxide (36.0 g, 0.564 mole), ethyl alcohol (200 g) were combined and reaction mixture was refluxed for three hours prior to quenching. Crude yield: 74.7%, distilled yield: 61.7%.

Flavor description: meaty, bloody.

HMNR: 1.25 ppm (d, 6H, J=6.85 Hz), 1.29 ppm (t, 3H, J=7.12 Hz), 1.52 ppm (s, 6H), 3.10 ppm (septet, 1H, J=6.85 Hz), 4.18 ppm (q, 2H, J=7.12 Hz).

Example II

Structure XI: Preparation of Ethyl 2-(Benzoylthio)-2-methyl propanoate

First, Ethyl 2-Acetylsulfanyl-2-methyl-propanoate was prepared as follows: Ethyl 2-bromoisobutyrate (100.0 g, 0.513 mole), thioactetic acid (42.9 g, 00564 mole), potassium hydroxide (36.0 g, 0.564 mole), ethyl alcohol (237.5 g), refluxed reaction mixture for six hours. 100% conversion was observed. The reaction mix was concentrated and added in the next step without purification for preparation of Ethyl 2-(Benzoylthio)-2-methyl propanoate.

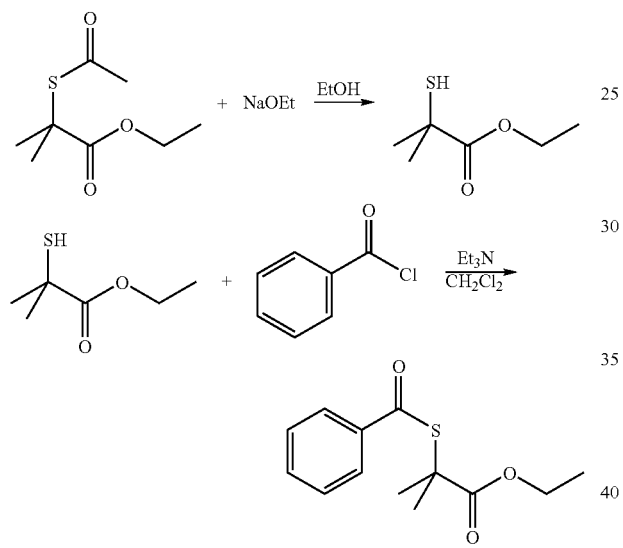

Second, using an ice bath, 170 mL of 21% sodium ethoxide (0.58 mole) ethanol solution was cooled down (less than 10° C.) in a three-neck round-bottomed flask with stirring. The Ethyl 2-Acetylsulfanyl-2-methyl-propanoate (100 g, 0.53 mole) was added dropwise over a period of 10-15 minutes. The reaction mixture was stirred for an additional 10 minutes following the addition with cooling and 1 hour at 23° C. The pH of the reaction mixture was adjusted to 6 with 10% hydrochloric acid then extracted using MTBE. The organic layer was washed with saturated sodium chloride solution, dried with sodium sulfate and concentrated. The crude was transferred to a three-neck round bottom flask which was cooled with an ice bath. Methylene chloride (500 mL) and triethyl amine (58.7 g, 0.58 mole) were added to the flask. With stirring, benzoyl chloride (81.5 g, 0.58 mole) was added dropwise and the temperature of the reaction mixture was below 5° C. The reaction mixture was stirred overnight at 23° C. following the addition. Wash the reaction mixture successively with saturated sodium chloride solution, 1N HCl, saturated sodium bicarbonate solution, and saturated sodium chloride solution, then dried with sodium sulfate and concentrated. The product was purified by vacuum distillation. Crude yield: 122%; distilled yield: 98.8%.

Flavor description: catty, tropical. Fragrance description: onion, fruity, oily, intense.

HMNR: 1.25 ppm (t, 3H, J=7.11 Hz); 1.69 ppm (s, 6H); 4.22 ppm (q, 2H, J=7.12 Hz); 7.42 ppm (m, 2H); 7.55 ppm (m, 1H); 7.90 ppm (m, 2H).

Example III

Flavor Evaluation

The following compounds, presented in the Table II below, were tested in a commercially available Peach Nectar drink with a formulation containing the following ingredients of water, peach pulp, high fructose corn syrup, food starch, citric acid, ascorbic acid, vitamin c and red 3.

The following compounds, presented in the Table II below, were tested in a commercially available Beef Broth with a formulation containing the following ingredients of beef stock, contains less then 1% of the following: salt, yeast extract, natural beef flavor, monosodium glutamate, caramel color, disodium inosinate, and disodium guanylate.

The compounds were used at the following levels in the peach nectar drink and Beef Broth:

Threshold level: 0.2 parts per billion.

Saturation level: 50 parts per billion.

Preferred usage level: 20 parts per billion to 10 parts per million.

The general consensus was that the thiols lend a catty, tropical note to the peach nectar, whereas, in the broth they lend a more serumy, bloody, and roasted characteristic.

TABLE II

| Compound | Concentration: | Peach Nectar | Beef Broth |
|---|---|---|---|
| Structure I | 10 ppb | added fuzziness of peach, tropical | carmelized onion |
| Structure II | 50 ppb | More tropical, fermented, prune-like, slightly catty. | bloody, serumy, liverwurst |
| Structure III | 500 ppb | fermented, candy-like | serumy, roast beef |

TABLE II-continued

| Compound | Concentration | Peach Nectar | Beef Broth |
|---|---|---|---|
| 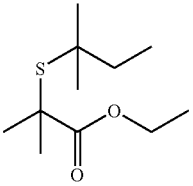<br>Structure IV | 5 ppm | fermented, catty, potentiated acid, more juice-like than nectar | bitter, burnt, floral, catty, peppery, roast beef |
| 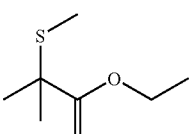<br>Structure V | 2 ppm | sweetened, delays acid, plum-like, grapey | rummy, peppercorns, liver |
| 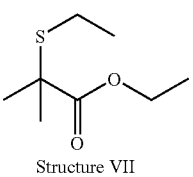<br>Structure VII | 25 ppb | tropical, catty, sulfurous | Onion characteristic |
| 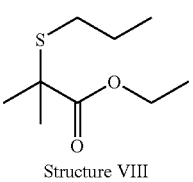<br>Structure VIII | 100 ppb | Potentiated acid, sweeter, slightly metallic, added "bite." | fullness |
| 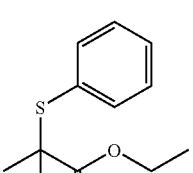<br>Structure IX | 10 ppm | More prune-like, sweeter, fermented, catty, berry | herbacious, tropical |
| 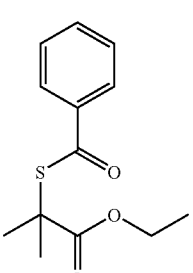<br>Structure XI | 500 ppb | catty, fermented | liverwurst, processed meats, serumy |

What is claimed is:

1. A method of flavoring a product comprising adding to the product a flavor composition comprising the compound defined according to structure:

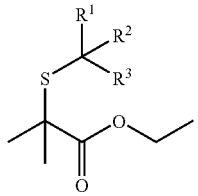

wherein $R^1$, $R^2$ and $R^3$ is independently selected from the group consisting of a $C_1$ to $C_4$ straight, branched or cyclic hydrocarbon moiety containing single and/or double bonds.

2. The method of claim 1 wherein the compound is present in the product in a concentration in a range of about 0.001 ppm to about 500 ppm.

3. The method of claim 1 wherein the compound is present in the product in a concentration in a range of about 0.01 ppm to about 50 ppm.

4. The method of claim 1 wherein the product is selected from the group consisting of a food product, a beverage product, an oral hygiene product, a pharmaceutical product, a chewing gum, and combination thereof.

5. The method of claim 4 wherein the food product is selected from the group consisting of a meat product, a vegetable product, and combinations thereof.

6. The method of claim 1 wherein the compound is selected from the group consisting of 2-t-Butylsulfanyl-2-methyl-propionic acid ethyl ester (Structure III) and 2-(1,1-Dimethyl-propylsulfanyl)-2-methyl-propionic acid ethyl ester (Structure IV).

7. A flavor composition comprising the compound of

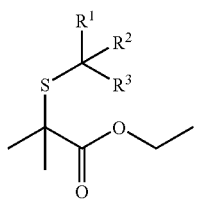

wherein $R^1$, $R^2$ and $R^3$ is independently selected from the group consisting of a $C_1$ to $C_4$ straight, branched or cyclic hydrocarbon moiety containing single and/or double bonds.

8. A flavor composition comprising a compound selected from the group consisting of 2-t-Butylsulfanyl-2-methyl-propionic acid ethyl ester (Structure III) and 2-(1,1-Dimethyl-propylsulfanyl)-2-methyl-propionic acid ethyl ester (Structure IV).

* * * * *